United States Patent [19]

Miller

[11] Patent Number: 4,657,713
[45] Date of Patent: Apr. 14, 1987

[54] HEATED RESPIRATORY THERAPY HUMIDIFIER

[75] Inventor: Kenneth G. Miller, Palatine, Ill.

[73] Assignee: Intertech Resources Inc., Bannockburn, Ill.

[21] Appl. No.: 719,886

[22] Filed: Apr. 3, 1985

Related U.S. Application Data

[62] Division of Ser. No. 496,103, May 19, 1983, Pat. No. 4,532,088.

[51] Int. Cl.[4] .................. A61M 16/18; B01F 3/04
[52] U.S. Cl. ......................... 261/142; 128/203.27; 219/273; 261/66; 261/104; 261/154; 261/DIG. 65
[58] Field of Search ............... 261/104, 107, 142, 154, 261/66, 71, 4–6, DIG. 65; 128/203.26, 203.27; 219/271–276; 210/175, 180, 181, 184; 55/259

[56] References Cited

U.S. PATENT DOCUMENTS

| | | | |
|---|---|---|---|
| 1,732,674 | 10/1929 | Dever | 261/142 X |
| 3,864,440 | 2/1975 | Giocoechea | 261/142 X |
| 3,912,795 | 10/1975 | Jackson | 261/104 X |
| 3,954,920 | 5/1976 | Heath | 261/104 |
| 4,101,294 | 7/1978 | Kimura | 261/104 X |
| 4,101,611 | 7/1978 | Williams | 261/DIG. 65 |
| 4,110,419 | 8/1978 | Miller | 261/DIG. 65 |
| 4,116,387 | 9/1978 | Kremer, Jr. et al. | 261/DIG. 65 |
| 4,216,176 | 8/1980 | Tanaka | 261/154 X |
| 4,288,396 | 9/1981 | Ottestad | 261/DIG. 65 |
| 4,481,986 | 11/1984 | Meyers | 261/DIG. 7 |

Primary Examiner—Richard L. Chiesa
Attorney, Agent, or Firm—Dressler, Goldsmith, Shore, Sutker & Milnamow, Ltd.

[57] ABSTRACT

A humidifier assembly is disclosed. Parts of the humidifier assembly may be disposable. The assembly comprises a housing, heater means on the housing, a liquid water supply means that communicates with the heater means, a hollow shell on the housing that defines a humidification chamber, and a filter means in the humidification chamber and positioned in juxtaposition with the surface of the heater means for passing water vapor into breathable gas. Preferably the filter means is hydrophobic.

6 Claims, 5 Drawing Figures

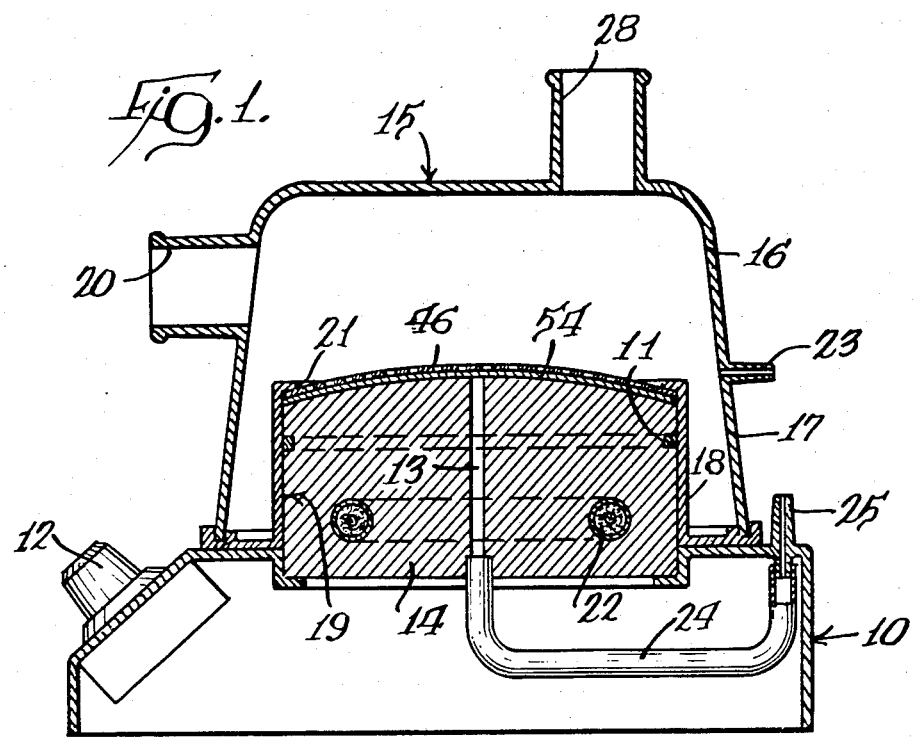
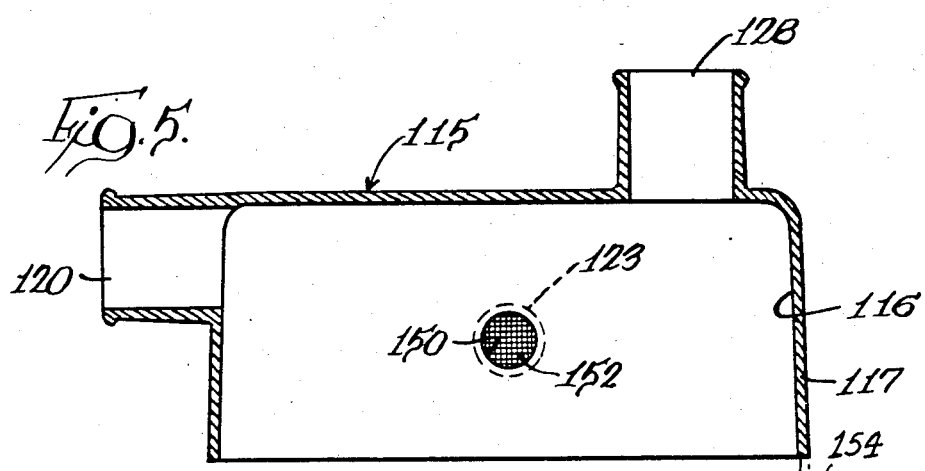
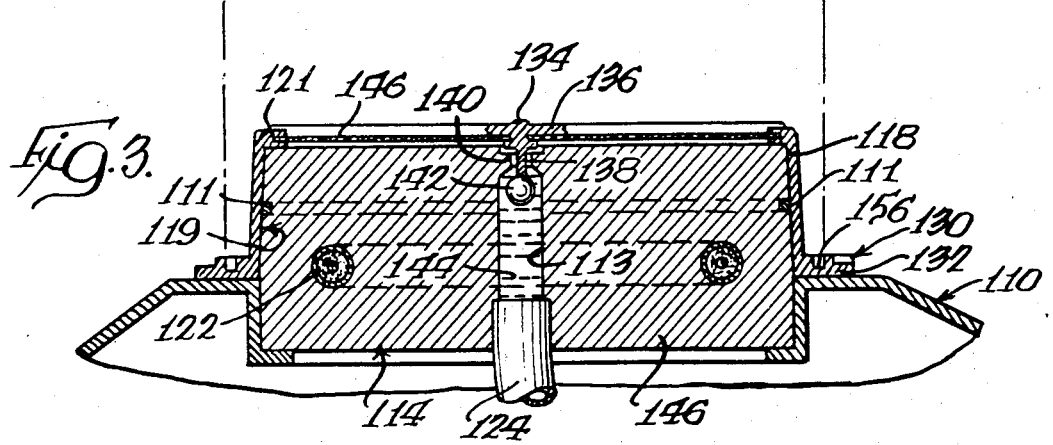

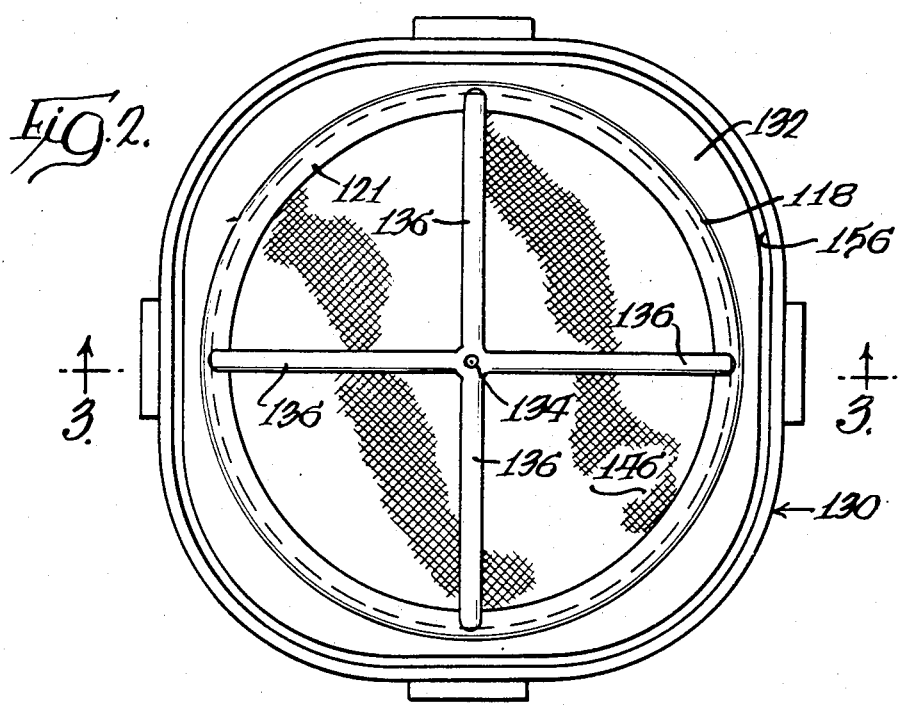
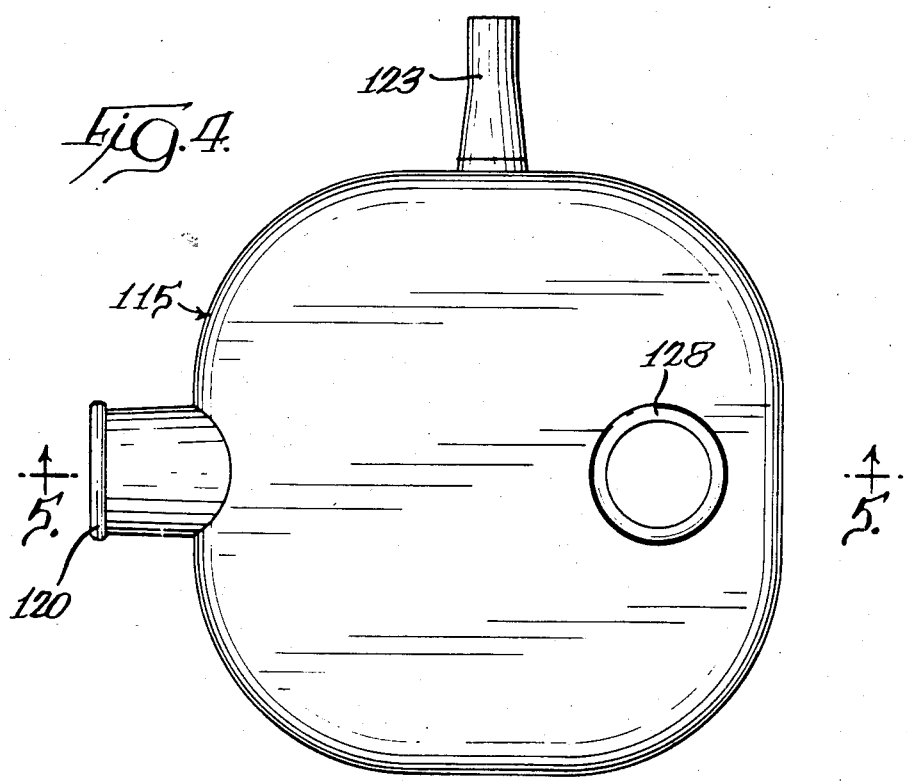

HEATED RESPIRATORY THERAPY HUMIDIFIER

This is a division of application Ser. No. 496,103, filed May 19, 1983, now U.S. Pat. No. 4,532,088.

BACKGROUND OF THE INVENTION

Several types of humidifying devices are presently available for adding humidity and heat to a breathable gas stream supplied to patients utilizing ventilators or undergoing inhalation therapy. Also, because some such patients have reduced breathing capability, each breath may be supplied mechanically directly to the trachea. However, when the natural membranes in the nose and mouth are bypassed, artificial humidification is required.

Existing systems for humidifying a breathable gas stream have one or more disadvantages. For example, systems of the type shown in U.S. Pat. No. 4,110,419 require a large sterile reservoir, usually disposable, which is not only expensive but also contributes greatly to pressure compliance of the system. Thus, the pre-filled, sterile water reservoirs expand and contract with the ventilator pressure. Further, a supply of such reservoirs takes up a great deal of storage space. Sterile water is also expensive, it sells for as much as several dollars a quart. These and other disadvantages are overcome or at least substantially minimized by the present invention.

SUMMARY OF THE INVENTION

The present invention provides an improved humidifier assembly for enhancing the moisture content of a breathable gas to be inhaled by a patient undergoing inhalation therapy. The humidifier assembly comprises a compact housing, and a special heater means and a hollow shell both mounted on the housing. The heater means has a generally horizontally disposed heater surface adapted to receive liquid water from a suitable liquid water supply in a direct heat transfer relationship. The hollow shell defines a humidification chamber and an inlet for a breathable gas. An outlet for humidified breathable gas is also provided.

The humidification chamber is in juxtaposition with respect to the heater surface. Liquid water from the liquid water supply may be conveyed to the heater surface for vaporization of said liquid water in the humidification chamber. Preferably the heater means projects upwardly into the humidification chamber so that the gas to be humidified sweeps past the heater surface on which water vaporization is effected. A filter assembly through which water to be added to the breathable gas passes is positioned between the liquid water supply and the humidification chamber.

In a preferred embodiment the filter assembly includes a relatively hydrophobic filter which is disposed closely adjacent the heater surface with liquid water being supplied to the heater surface from below the filter assembly so that only water vapor passes upwardly therethrough and into the humidifier chamber.

Further objects, features and advantages of this invention will become apparent from the following description and drawings.

BRIEF DESCRIPTION OF THE DRAWINGS

FIG. 1 is an elevational view, in cross-section, illustrating a humidifier assembly embodying this invention;

FIG. 2 is a plan view of a filter base assembly utilized in a preferred embodiment of this invention;

FIG. 3 is a fragmentary sectional elevation of the filter base assembly taken along plane 3—3 in FIG. 2;

FIG. 4 is a plan view of a hollow shell that defines the humidification chamber and fits over the filter base assembly shown in FIGS. 2 and 3; and FIG. 5 is sectional elevation of the hollow shell taken along plane 5—5 in FIG. 4.

DETAILED DESCRIPTION OF PREFERRED EMBODIMENTS

This invention can be practiced and used in many different forms. The specification and accompanying drawings disclose specific embodiments that illustrate the invention. This invention is not intended to be limited to the specific embodiments illustrated, however.

Housing 10 supports an upstanding, pedestal-like heater means 14 and an associated humidification chamber 16 defined by hollow shell 15 fitted onto housing 10. Temperature control knob 12 is also mounted on housing 10.

The heater means 14 defines a liquid water passage 13 which is connected to and communicates with water supply inlet nozzle 25 by means of flexible conduit 24. Water can be supplied to inlet nozzle 25 in any suitable manner, such as from an external liquid water source, e.g., an associated reservoir (not shown). Nozzle 25 can also be in the form of a cannula or spike adapted to penetrate a sealing membrane of a water bottle that serves as the external liquid source.

Shell 15 includes a downwardly depending sleeve portion 17 which, together with hollow skirt portion 18, defines a central cavity 19 in which heater means 14 is positioned. Sleeve portion 17, via a seal, such as an "O" ring 11, sealingly surrounds the heater means 14 and permits the interchange of the hollow shells such as shell 15. Skirt portion 18 terminates in an inwardly extending flange 21 which supports a filter element 46, preferably a hydrophobic filter element, so that it confronts the associated upper surface of the heater means. To facilitate the distribution of liquid water thereover, the upper heater surface can be provided with a slight crown, but it is not essential to do so. When filter element 46 is hydrophobic, only water vapor can pass upwardly therethrough.

Shell 15 further defines a gas inlet 28 and a humidified gas outlet 20. Vent 23 communicates with the external associated liquid water source and provides pressure equalization therewith as well as flow control as will be discussed below.

In use, in the humidifier assembly of FIG. 1 water is flowing from water inlet 15 upwardly to hydrophobic filter 46. As the water passes upwardly through passage 13 it is preheated by the action of resistance heating element 22. If the heater means is operated at a relatively high temperature so that too much heat is transferred to the liquid water in passage 13, this passage may be partially insulated by a sleeve, e.g., a tetrafluoroethylene tube, that limits the rate of heat transfer thereacross. The upper heated surface of heater means 14 evaporates the water distributed thereon, while liquid water entry into the chamber 16 is precluded. Water vapor, however, is freely transmitted upwardly into humidification chamber 16 through filter 46 for humidification of the dry breathable gas. Optionally, a wicking layer 54 can be provided between heater means 14 and the hydrophobic filter 46. The wicking layer or the filter can be used to control water flow rate to the heater means, if desired.

Liquid level back-up control in the event of filter rupture is accomplished by vent 23 which, when occluded by water, prevents venting and therefore prevents liquid flow from the external reservoir (via the water inlet) to the heater means 14. Again, it is not necessary to use sterile water since the pore size of filter 46 can be selected so as to exclude contaminants such as bacteria from the humidification chamber. Distilled water, or even tap water, may be used.

A preferred embodiment of the present invention is illustrated in FIGS. 2 through 5, inclusive. Referring to FIGS. 2 and 3 in particular, filter base assembly 130 that can be removably positioned over heater 114 includes base flange 132 unitary with upstanding skirt portion 118 and inwardly extending peripheral flange 121. Hydrophobic filter element 146 is mounted in filter base assembly 130 at flange 121 and at juncture 134 of radially extending filter retaining members 136 that connect with peripheral flange 121. Nipple 138 projects from juncture 134 and extends into the heater-receiving cavity defined by skirt portion 18.

Heater 114 is provided with a relatively flat, substantially horizontal upper surface or plateau adapted to receive and distribute liquid water. Additionally, heater 114 defines central passageway 113 that communicates with an external liquid water supply via conduit 124 adjacent to the upper surface of heater 114. A peripheral protuberance 140 extends into passageway 113 from heater block 146 and defines a valve seat for a check valve such as ball valve 142 situated within passageway 113.

Ball valve 142 is lighter than water, i.e., it has a specific gravity less than one, preferably about 0.4 to about 0.6. Thus, when an aliquot 144 of liquid water is present in passageway 113, the buoyancy of water urges ball valve 142 against the valve seat defined by peripheral protuberance 140 if the filter base assembly 130 is not in place, thereby precluding liquid water spillage. On the other hand, when filter base assembly 130 is positioned over heater 114, nipple 138 abuts ball valve 142 and is sufficiently long to prevent ball valve 142 from sealing passageway 113, thereby permitting liquid water flow to the upper surface of heater 114 and to hydrophobic filter 146. In an alternative embodiment the ball valve can be heavier than water, in which event ball valve is urged against the valve seat by means of a biasing spring.

In either case, the check valve can be incorporated as part of the heater means, or the check valve can be made as a separate sub-assembly, e.g. within a tube of a relatively heat-resistant material which tube is then positioned within passageway 113 as a unit. In the latter instance, protuberance 140 can be made integral or unitary with the inserted tube as desired.

Circumferential O-ring 111 provides a liquid-tight seal between heater 114 and the inner surface of skirt portion 118. Resistance heater element 122 in heater block 146 provides the desired energy input to vaporize the required amount of liquid water.

Shell 115 (FIGS. 4 and 5) defines the humidification chamber and is provided with side outlet port 120 and top inlet port 128. Additionally, vent nozzle 123, serving the same function as nozzle 23 described above in connection with embodiment illustrated in FIG. 1, is provided on shell 115. Preferably, a hydrophobic filter element 152 is provided across the venting port 150 for nozzle 123.

The lower rim 154 of sleeve portion 117 is received in groove 156 defined in base flange 132. Shell 115 can thus be mounted onto filter base assembly 130 to provide a humidification canister. If it is desired to provide a complete, disposable canister in a sterile package, the lower rim 154 of shell 115 is permanently bonded to base flange 132. In the alternative, shell 115 can be sterilizable and thus non-disposable, and only filter base assembly 130 can be a disposable item. In the latter case, rim 154 is removably received into groove 156. If desired, rim 154 and base flange 132 can be provided with mating threads or a bayonet-type interlock to removably secure shell 115 to filter base asembly 130.

In a yet another variant, filter element 146 can be provided with a separate peripheral frame that is removably attachable, e.g. by means of thread or lugs, to skirt portion 118 and thus is independently replaceable as required. In such an event, shell 115 and filter base assembly can be sterilizable and thus non-disposable and can be permanently or removably joined to one another.

The overall operation of the humidifier illustrated in FIGS. 2 through 5, inclusive, is substantially the same as that described hereinabove for the embodiment of FIG. 1. However, the preferred embodiment shown in FIGS. 2 through 5 further provides the liquid water flow interrupt featured by the coaction of nipple 138, and a check valve that includes valve seat 140 and ball valve 142.

While any heat-resistant filtering material can be used for filters 46 and 146 as long as the pore size selected is sufficient to prevent undesirable contaminants from entering the humidification chamber, the use of a hydrophobic filter material is preferred. When a hydrophobic filter material is used, only water vapor can enter the humidification chamber and the entrainment of water droplets by the gas stream passing through the chamber is avoided. Additionally, a hydrophobic filter material provides a convenient means for controlling the flow of liquid water to the upper heater surface for vaporization as well as for elimination of any air bubbles trapped between the filter and the adjacent heater surface.

Hydrophobic filter materials suitable for present purposes are available commercially. For use in humidifiers embodying the present invention a pore size of about 0.02 to about 0.5 micrometers ($\mu$m is preferred; however, the pore size can be smaller or larger, as desired, depending on the potential contaminants that are to be excluded and the filter flow-through rate that is desired.

Particularly preferred filter materials for use in the filters contemplated by the present invention are microporous expanded polytetrafluoroethylene structures having a matrix of nodules interconnected with fibrils. Alternatively, membrane filters that are inherently hydrophobic or fibrous mats treated with a water repellent substance can be used.

The degree of porosity of the filter material can be selected to meet the contemplated throughput requirements. Preferably the porosity is such as to be capable of providing a flow rate equivalent to about 1–5 liters of air per minute per square centimeter as a pressure of about 10 pounds per square inch (about 0.7 kilograms per square centimeter).

The foregoing discussion and illustrations are intended as examples of the present inventive concept and are not to be construed as limitations thereof. Still other variations and rearrangements of parts within the spirit and scope of this invention are possible and will present themselves to those skilled in the art.

I claim:

1. A disposable canister for use in a humidifier assembly for humidifying a breathable gas to be inhaled by a patient undergoing inhalation therapy; said humidifier assembly including a heater means mounted on a housing and having an exposed heated surface adapted to receive liquid water in direct heat transfer relationship therewith, and liquid water supply means for the exposed heated surface; and said canister comprising a hollow shell having an open end adapted for removably mounting on said housing and provided with a gas inlet and a gas outlet; and a porous, vapor-permeable but hydrophobic filter membrane mounted within said hollow shell across said open end but at a position substantially uniformly spaced from said open end and said exposed heated surface when the shell is mounted on said housing;

said hollow shell together with said hydrophobic filter membrane together defining a humidification chamber on one side of the filter membrane that communicates with the gas inlet and the gas outlet in the shell and through which said breathable gas is adapted to pass between the inlet and the outlet, and defining a heater-receiving cavity on the other side of the filter membrane.

2. The disposable canister in accordance with claim 1 wherein the porous, water vapor-permeable portion has a pore size of about 0.02 to about 0.5 micrometers.

3. The disposable canister in accordance with claim 1 wherein said humidification chamber is provided with a vent.

4. The disposable canister in accordance with claim 3 wherein the vent includes a hydrophobic filter element.

5. The disposable canister in accordance with claim 1 further including a base assembly for the canister adapted for removable positioning over the heater means; said base assembly including a projecting nipple for actuating a valve on said heater means.

6. The disposable canister in accordance with claim 1 wherein the hydrophobic filter membrane is a microporous expanded polytetrafluoroethylene structure having a matrix of nodules interconnected with fibrils and has a pore size of about 0.02 to about 0.5 micrometers.

* * * * *